United States Patent
Sowelam

(10) Patent No.: US 9,247,883 B2
(45) Date of Patent: Feb. 2, 2016

(54) DETECTING WORSENING HEART FAILURE BASED ON FLUID ACCUMULATION WITH RESPIRATORY CONFIRMATOIN

(71) Applicant: Medtronic, Inc., Minneapolis, MN (US)

(72) Inventor: Sameh Sowelam, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/155,416

(22) Filed: Jan. 15, 2014

(65) Prior Publication Data

US 2014/0128749 A1    May 8, 2014

Related U.S. Application Data

(63) Continuation of application No. 12/363,264, filed on Jan. 30, 2009, now Pat. No. 8,632,473.

(30) Foreign Application Priority Data

Jan. 28, 2010    (WO) ................ PCT/US2010/022352

(51) Int. Cl.
| | | |
|---|---|---|
| *A61B 5/0205* | (2006.01) | |
| *A61N 1/39* | (2006.01) | |
| *A61N 1/365* | (2006.01) | |
| *A61B 5/00* | (2006.01) | |
| *A61B 5/0245* | (2006.01) | |

(Continued)

(52) U.S. Cl.
CPC ............. *A61B 5/0205* (2013.01); *A61B 5/0245* (2013.01); *A61B 5/053* (2013.01); *A61B 5/0537* (2013.01); *A61B 5/0538* (2013.01); *A61B 5/0809* (2013.01); *A61B 5/0816* (2013.01); *A61B 5/4836* (2013.01); *A61B 5/4878* (2013.01); *A61B 5/7275* (2013.01); *A61N 1/36521* (2013.01); *A61N 1/3962* (2013.01)

(58) Field of Classification Search
None
See application file for complete search history.

(56) References Cited

U.S. PATENT DOCUMENTS

| | | |
|---|---|---|
| 4,374,382 A | 2/1983 | Markowitz |
| 4,823,797 A | 4/1989 | Heinze et al. |

(Continued)

FOREIGN PATENT DOCUMENTS

| | | |
|---|---|---|
| EP | 1997427 A1 | 4/2008 |
| WO | 9833554 | 8/1998 |

(Continued)

OTHER PUBLICATIONS

Office Action from U.S. Appl. No. 12/184,003, dated Dec. 21, 2011, 11 pp.

(Continued)

*Primary Examiner* — Shanon A Foley
(74) *Attorney, Agent, or Firm* — Carol F. Barry

(57) ABSTRACT

A medical device monitors a level of fluid accumulation, e.g., pulmonary edema, and one or more respiratory parameters of the patient to detect worsening heart failure. The medical device may use intrathoracic impedance measurements to monitor both the fluid accumulation and the one or more respiratory parameters. Respiration rate and volume, also referred to as the tidal volume, are examples of respiratory parameters. The medical device examines the one or more respiratory parameters after determining that the fluid accumulation indicates worsening heart failure. In this manner, the medical device uses the one or more respiratory parameters to confirm a determination of worsening heart failure that was made based on the fluid accumulation.

14 Claims, 10 Drawing Sheets

(51) Int. Cl.
 *A61B 5/053* (2006.01)
 *A61B 5/08* (2006.01)

(56) References Cited

U.S. PATENT DOCUMENTS

| | | |
|---|---|---|
| 5,107,833 A | 4/1992 | Barsness |
| 5,117,824 A | 6/1992 | Keimel et al. |
| 5,168,871 A | 12/1992 | Grevious |
| 5,271,395 A | 12/1993 | Wahlstrand et al. |
| 5,292,343 A | 3/1994 | Blanchette et al. |
| 5,314,450 A | 5/1994 | Thompson |
| 5,324,315 A | 6/1994 | Grevious |
| 5,354,319 A | 10/1994 | Wyborny et al. |
| 5,383,909 A | 1/1995 | Keimel |
| 5,545,186 A | 8/1996 | Olson et al. |
| 5,749,367 A | 5/1998 | Gamlyn et al. |
| 5,755,736 A | 5/1998 | Gillberg et al. |
| 5,836,975 A | 11/1998 | DeGroot |
| 5,876,353 A | 3/1999 | Riff |
| 5,957,861 A | 9/1999 | Combs et al. |
| 6,045,513 A | 4/2000 | Stone et al. |
| 6,102,874 A | 8/2000 | Stone et al. |
| 6,104,949 A | 8/2000 | Crick et al. |
| 6,148,233 A | 11/2000 | Owen et al. |
| 6,154,674 A | 11/2000 | Meier |
| 6,221,011 B1 | 4/2001 | Bardy |
| 6,263,243 B1 | 7/2001 | Lang |
| 6,277,072 B1 | 8/2001 | Bardy |
| 6,280,380 B1 | 8/2001 | Bardy |
| 6,280,409 B1 | 8/2001 | Stone et al. |
| 6,336,903 B1 | 1/2002 | Bardy |
| 6,405,085 B1 | 6/2002 | Graupner et al. |
| 6,449,509 B1 | 9/2002 | Park et al. |
| 6,459,929 B1 | 10/2002 | Hopper et al. |
| 6,463,326 B1 | 10/2002 | Hartley et al. |
| 6,473,640 B1 | 10/2002 | Erlebacher |
| 6,480,733 B1 | 11/2002 | Turcott |
| 6,512,949 B1 | 1/2003 | Combs et al. |
| 6,572,557 B2 | 6/2003 | Tchou et al. |
| 6,595,927 B2 | 7/2003 | Pitts-Crick et al. |
| 6,671,549 B2 | 12/2003 | Van Dam et al. |
| 6,821,249 B2 | 11/2004 | Casscells, III et al. |
| 6,866,629 B2 | 3/2005 | Bardy |
| 6,895,275 B2 | 5/2005 | Markowitz et al. |
| 6,907,288 B2 | 6/2005 | Daum |
| 6,931,272 B2 | 8/2005 | Burnes |
| 6,945,934 B2 | 9/2005 | Bardy |
| 6,960,167 B2 | 11/2005 | Bardy |
| 7,127,290 B2 | 10/2006 | Girouard et al. |
| 7,177,681 B2 | 2/2007 | Zhu et al. |
| 7,184,821 B2 | 2/2007 | Belalcazar et al. |
| 7,248,916 B2 | 7/2007 | Bardy |
| 7,272,442 B2 | 9/2007 | Freeberg |
| 7,308,309 B1 | 12/2007 | Koh |
| 7,310,551 B1 | 12/2007 | Koh et al. |
| 7,313,434 B2 | 12/2007 | Belalcazar et al. |
| 7,340,296 B2 | 3/2008 | Stahmann et al. |
| 7,387,610 B2 | 6/2008 | Stahmann et al. |
| 7,389,143 B2 | 6/2008 | Hopper et al. |
| 8,180,440 B2 | 5/2012 | McCombie et al. |
| 2001/0011153 A1 | 8/2001 | Bardy |
| 2001/0021801 A1 | 9/2001 | Bardy |
| 2001/0039504 A1 | 11/2001 | Linberg et al. |
| 2002/0026104 A1 | 2/2002 | Bardy |
| 2003/0028221 A1 | 2/2003 | Zhu et al. |
| 2003/0055461 A1 | 3/2003 | Girouard et al. |
| 2003/0125611 A1 | 7/2003 | Bardy |
| 2003/0149367 A1 | 8/2003 | Kroll et al. |
| 2003/0220580 A1 | 11/2003 | Alt |
| 2004/0102712 A1 | 5/2004 | Belalcazar et al. |
| 2004/0122484 A1 | 6/2004 | Hatlestad et al. |
| 2004/0148140 A1 | 7/2004 | Tarassenko et al. |
| 2004/0167580 A1 | 8/2004 | Mann et al. |
| 2004/0172080 A1 | 9/2004 | Stadler et al. |
| 2005/0124908 A1 | 6/2005 | Belalcazar et al. |
| 2006/0020295 A1 | 1/2006 | Brockway et al. |
| 2006/0094967 A1 | 5/2006 | Bennett et al. |
| 2006/0293609 A1 | 12/2006 | Stahmann et al. |
| 2007/0021678 A1 | 1/2007 | Beck et al. |
| 2007/0142732 A1 | 6/2007 | Brockway et al. |
| 2007/0156061 A1 | 7/2007 | Hess |
| 2007/0203423 A1 | 8/2007 | Bardy |
| 2008/0024293 A1 | 1/2008 | Stylos |
| 2008/0027349 A1 | 1/2008 | Stylos |
| 2008/0082001 A1 | 4/2008 | Hatlestad et al. |
| 2008/0161657 A1* | 7/2008 | Bullens et al. ............ 600/301 |
| 2010/0030292 A1 | 2/2010 | Sarkar et al. |
| 2010/0030293 A1 | 2/2010 | Sarkar et al. |
| 2010/0114241 A1 | 5/2010 | Donofrio et al. |
| 2010/0198097 A1 | 8/2010 | Sowelam |

FOREIGN PATENT DOCUMENTS

| | | |
|---|---|---|
| WO | 0064336 A1 | 11/2000 |
| WO | 0132260 A1 | 5/2001 |
| WO | 2006070124 A1 | 7/2006 |
| WO | 2006081432 A1 | 8/2006 |
| WO | 2007079354 A2 | 7/2007 |

OTHER PUBLICATIONS

Office Action from U.S. Appl. No. 12/184,149, dated Sep. 30, 2011, 6pp.

Response to Office Action dated Sep. 30, 2011, from U.S. Appl. No. 12/184,149, filed Dec. 12, 2011, 14pp.

Advisory Action from U.S. Appl. No. 12/184,003, dated Apr. 5, 2012, 3pp.

Notice of Allowance from U.S. Appl. No. 12/184,149, dated Jun. 8, 2012, 7pp.

Notice of Allowance from U.S. Appl. No. 12/768,384, dated Jun. 19, 2012, 11pp.

International Search Report and Written Opinion from PCT Application Serial No. PCT/US2010/054539 dated Feb. 4, 2011 (11 pages).

Response to Office Action dated Jan. 27, 2012, from U.S. Appl. No. 12/184,149, filed Apr. 25, 2012, 13pp.

Response to Office Action dated Dec. 21, 2011, from U.S. Appl. No. 12/184,003, filed Feb. 21, 2012, 7pp.

Office Action from U.S. Appl. No. 12/184,149, dated Jan. 27, 2012, 7pp.

Office Action from U.S. Appl. No. 12/184,003, dated Jun. 28, 2011, 11pp.

Response to Office Action dated Jun. 28, 2011, from U.S. Appl. No. 12/184,003, filed Sep. 28, 2011, 15pp.

Office Action from U.S. Appl. No. 12/184,149, dated Apr. 7, 2011, 7pp.

Response to Office Action dated Apr. 7, 2011, from U.S. Appl. No. 12/184,149, filed Jul. 7, 2011, 20pp.

(PCT/US2010/022352) PCT Notification of Transmittal of the International Search Report and Written Opinion of the International Searching Authority.

U.S. Appl. No. 12/148,003, filed Jul. 31, 2008, entitled "Using Multiple Diagnostic Parameters for Predicting Heart Failure Events", by Sarkar et al.

International Search Report and Written Opinion from corresponding PCT Application Serial No. PCT/US2008/009307, mailed May 8, 2009 (11pgs.).

Adamson et al, "Continuous Autonomic Assessment in Patients with Symptomatic Heart Rate Failure: Prognostic Value of Heart Rate Variability Measured by an Implanted Cardiac Resynchronization Device", Circulation Journal of American Heart Association, pp. 2389-2394, 110:16, Lippincott Williams & Wilkins, Baltimore MD, 2004.

(56) References Cited

OTHER PUBLICATIONS

Baer et al. "Electronic Home Monitoring of Congestive Heart Failure Patients: Design and Feasibility", Congestive Heart Failure, 5:105-113, 1999.

Berman et al. "Transthoracic Electrical Impedance as a Guide to Intravascular Overload", Archives Surgery, 102, pp. 61-64 Jan. 1971.

Lusignan et al. "Compliance and Effectiveness of 1 Year's Home Telemonitoring. The Report of a Pilot Study of Patients with Chronic Heart Failure" European Journal of Heart Failure, 3:723-730, 2001.

Wuerz et al. "Effects of Prehospital Medications on Mortality and Length of Stay in Congestive Heart Failure", Annals of Emergency Medicine 21:6 pp. 669-674, Jun. 1992.

* cited by examiner

DETECTING WORSENING HEART FAILURE BASED ON FLUID ACCUMULATION WITH RESPIRATORY CONFIRMATOIN

RELATED APPLICATION

This application is a continuation of U.S. patent application Ser. No. 12/363,264, filed Jan. 30, 2009 entitled "DETECTING WORSENING HEART FAILURE BASED ON FLUID ACCUMULATION WITH RESPIRATORY CONFIRMATION", herein incorporated by reference in its entirety.

TECHNICAL FIELD

The invention relates to medical devices and, more particularly, medical devices for monitoring heart failure.

BACKGROUND

Generally, the first indication of worsening heart failure is significant swelling or breathing difficulties that cause the patient to visit a clinic, or be transported to a hospital on an emergency basis. By this point, cardiac decompensation may have progressed to a point requiring patient hospitalization. Accordingly, a variety of medical devices have been used, or proposed for use, to monitor heart failure, detect heart failure events, and provide an alert to the patient to seek medical treatment prior to the onset of worsening heart failure with symptoms that require hospitalization, such as severe pulmonary edema. Typically, such medical devices have been implantable. In many cases, such devices have been cardiac pacemakers, cardioverters, and/or defibrillators with added heart failure monitoring functionality.

Some medical devices have monitored heart failure by monitoring intrathoracic impedance. Intrathoracic impedance may generally provide an indication of the level of edema in patients. Worsening heart failure may result in cardiac chamber dilation, increased interstitial fluid volume, and pulmonary edema—all of which contribute to a decrease in intrathoracic impedance.

SUMMARY

This disclosure describes techniques for detecting worsening heart failure in a patient. A medical device monitors the level of fluid accumulation, and one or more respiratory parameters of the patient to detect worsening heart failure. The medical device uses intrathoracic impedance measurements to monitor both the fluid accumulation and the one or more respiratory parameters. Respiration rate and tidal volume are examples of respiratory parameters.

Although intrathoracic impedance decreases with increasing fluid accumulation, a decrease in intrathoracic impedance is not specific to fluid accumulation. For this reason, detecting worsening heart failure based on the intrathoracic impedance alone may result in false positives. Treating false positives, e.g., with diuretics, may result in diuresis leading to dehydration. Placing a heart failure patient in a hypovolumic state could cause a fall in cardiac output and lead to a heart failure related decompensation. Additionally, the purpose of using a medical device to provide early detection of worsening heart failure is to reduce the workload of a physician and to reduce the need for hospitalization. Early detection of a worsening condition may give the physician a chance to treat the patient prior to admission to a hospital. Detection algorithms that produce false positives may, in some cases, increase the burden on the health care providers.

Pulmonary edema has been associated with dyspnea, or breathlessness. Dyspnea causes an increase in respiration rate and a reduction in respiration volume. To reduce false positives after detecting fluid build-up, a medical device or secondary sensor examines one or more respiratory parameters, such as respiration rate and volume. The medical device uses the one or more respiratory parameters to confirm a determination of worsening heart failure made based on fluid accumulation alone. In some examples, the medical device is equipped with another sensor, such as a single-axis or multi-axis accelerometer, capable of sensing patient activity. Dyspnea detection would then be performed only when the patient is at rest to eliminate the possibility of misclassifying activity-induced breathlessness as dyspnea.

By confirming an indication of worsening heart failure using respiratory parameters, the device may more accurately detect worsening heart failure, i.e., detect worsening heart failure while producing fewer false positives. Moreover, because both fluid accumulation and the one or more respiratory parameters may be monitored based on transthoracic impedance measurements, an existing, e.g., implanted, device capable of monitoring transthoracic impedance may be modified to implement the techniques described herein.

In one example, the disclosure provides a method comprising monitoring, by a medical device, thoracic fluid accumulation in a patient, and determining, by the medical device, that the fluid accumulation indicates worsening heart failure in the patient. The method further comprises, in response to the determination that the fluid accumulation indicates worsening heart failure, monitoring, by the medical device, at least one respiratory parameter of the patient based on the impedance measurements, and determining, by the medical device, whether the respiratory parameter indicates worsening heart failure in the patient.

In another example, the disclosure provides a medical system comprising a fluid accumulation monitor configured to monitor thoracic fluid accumulation in a patient, and a detection module configured to detect worsening heart failure in the patient, wherein the detection module is configured to determine that the fluid accumulation indicates worsening heart failure in the patient. The medical system further comprises a respiratory monitor configured to monitor at least one respiratory parameter of the patient in response to the determination that the fluid accumulation indicates worsening heart failure. The detection module is further configured to determine whether the respiratory parameter indicates worsening heart failure in the patient in response to the determination that the fluid accumulation indicates worsening heart failure.

In another example, the disclosure provides a medical system comprising a medical system comprising means for monitoring thoracic fluid accumulation in a patient, means for determining that the fluid accumulation indicates worsening heart failure in the patient, means for monitoring at least one respiratory parameter of the patient in response to the determination that the fluid accumulation indicates worsening heart failure, and means for determining whether the respiratory parameter indicates worsening heart failure in the patient in response to the determination that the fluid accumulation indicates worsening heart failure.

DETAILED DESCRIPTION

Figure 1:
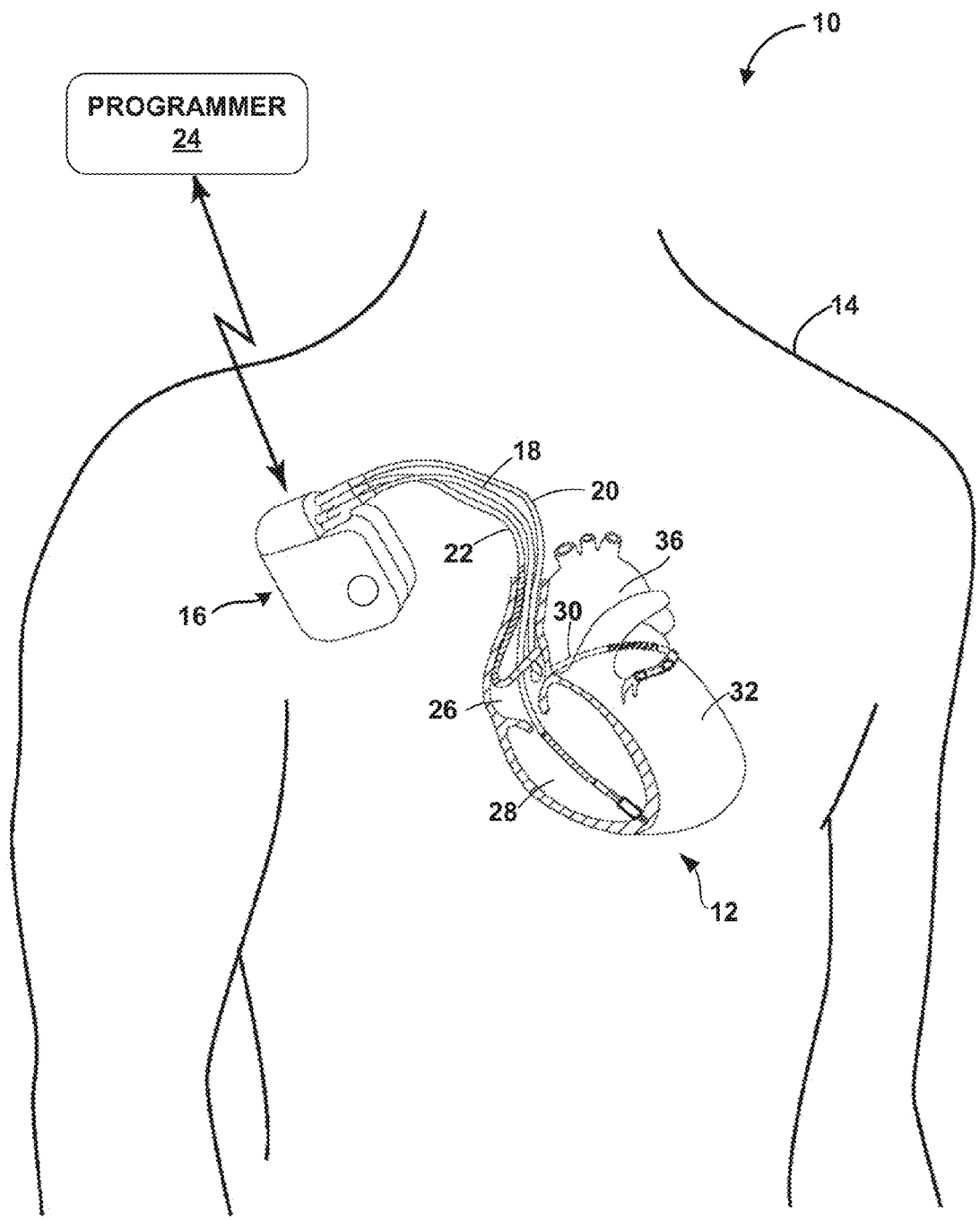
FIG. 1 is a conceptual diagram illustrating an example system that monitors the fluid accumulation and one or more respiratory parameters of a patient to detect worsening heart failure.

FIG. 1 is a conceptual diagram illustrating an example system 10 that monitors the fluid accumulation and one or more respiratory parameters of a patient 14 to detect worsening heart failure in the patient. System 10 may generate an alert in response to detecting worsening heart failure, so that patient 14 can seek appropriate treatment before experiencing a heart failure hospitalization (HFH) event. In some examples, system 10 may be configured to provide therapy to patient 14 and, in such examples, may deliver therapy or change therapy settings in response to detecting worsening heart failure in patient 14.

System 10 includes implantable medical device (IMD) 16, which is coupled to leads 18, 20, and 22, and a programmer 24. In some examples, IMD 16 may be a purely diagnostic device that monitors the fluid accumulation and one or more respiratory parameters to detect worsening heart failure in patient 14. In other examples, IMD 16 may additionally operate as a therapy delivery device that delivers electrical signals to heart 12 via one or more of leads 18, 20, and 22, such as an implantable pacemaker, a cardioverter, and/or defibrillator.

In still other examples, an IMD that monitors the fluid accumulation and one or more respiratory parameters of a patient to detect worsening heart failure may additionally deliver therapeutic substances to patient 14 via catheters (not shown). Moreover, a medical device that monitors the fluid accumulation and one or more respiratory parameters of a patient to detect worsening heart failure need not be implanted as shown in FIG. 1. As an example, such a medical device be implanted subcutaneously in patient 14, or may be an entirely external device with leads attached to the skin of patient 14 or implanted percutaneously in patient 14. In some examples, a medical device that monitors the fluid accumulation and one or more respiratory parameters need not include leads, but may include a plurality of electrodes on the housing of the medical device.

In some examples, IMD 16 is configured to collect intrathoracic impedance measurements for patient 14, and monitor the fluid accumulation and one or more respiratory parameters of patient 14 based on the impedance measurements. In other examples, other techniques or sensors for monitoring the fluid accumulation and one or more respiratory parameters may be employed. IMD 16 employs an algorithm to detect worsening heart failure based on the fluid accumulation and respiratory parameters. The algorithm is described in greater detail below and in FIG. 9.

Decreasing intrathoracic impedance indicates an accumulation of fluid. In one example, IMD 16 uses a fluid index as a measure of the fluid status of patient 14. The fluid index reflects a level of fluid accumulation, e.g., pulmonary edema. When the fluid index indicates worsening heart failure in patient 14, e.g., by crossing a threshold value, IMD 16 examines the one or more respiratory parameters to confirm whether patient 14 is experiencing worsening heart failure. The threshold value may be a predetermined value that is loaded into memory of IMD 16, a value programmed into IMD 16 by a clinician, or a value automatically calculated by IMD 16 based on impedance measurements post implant. In any case, when the fluid index is greater than the threshold value, IMD 16 triggers monitoring the impedance signal to determine respiratory parameters.

IMD 16 also uses the intrathoracic impedance measurements to monitor the one or more respiratory parameters, e.g., respiration rate and volume. In particular, an increased respiration rate and reduced respiration volume may indicate the presence of dyspnea and worsening heart failure. Accordingly, IMD 16 may detect and alert patient 14 of worsening heart failure when the fluid index and one or both of the respiration rate and volume indicate worsening heart failure.

In some examples, once respiration monitoring is triggered, IMD 16 continuously monitors respiratory parameters for a predetermined period of time, such as a couple of hours, a few days, or a week. During this time, IMD 16 may continue to monitor the fluid index and, if at any time, the fluid index drops below the threshold value, IMD 16 may cease to monitor the respiratory parameters. In some examples, IMD 16 compares the measured values for the respiratory parameters to corresponding baseline values, or thresholds derived from such baseline values. In some examples, IMD 16 initially determines a baseline or reference value for respiration rate and volume upon, or shortly after, implant. In some examples, IMD 16 determines baseline or reference values only after a predetermined time following implant, because intrathoracic impedance may change substantially for the first ninety or so days following implant.

In some examples, IMD 16 and/or programmer 24 are configured to provide an alert in response to detecting worsening heart failure in patient 14. The alert may be audible, visual, or tactile, and enables patient 14 to seek medical attention to treat the condition prior to experiencing a heart failure event, or a clinician to direct patient 14 to do so. In some examples, the alert is a silent alert transmitted to another device associated with a clinician or other user, such as a silent alert transmitted to a server and relayed to a physician computing device via a network.

IMD 16 collects intrathoracic impedance via electrodes located on leads 18, 20 and 22, and/or on the housing of IMD 16. Leads 18, 20 and 22 extend into the heart 12 of patient 14. Right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. In one example, IMD 16 measures intrathoracic impedance by creating an electrical path between a defibrillation coil on RV lead 18 and an electrode on the housing of IMD 16.

Other configurations, i.e., number and position of leads, are possible. In some examples, system 10 may include an additional lead or lead segment having one or more electrodes positioned at different locations in the cardiovascular system or chest cavity, such as within one of the vena cava, subcutaneously at a location substantially opposite IMD 16 vis-à-vis the thorax of patient 14, or epicardially, for measuring intrathoracic impedance.

Programmer 24 is, for example, a handheld computing device, computer workstation, or networked computing device. A user, such as a physician, technician, surgeon, electrophysiologist, or other clinician, interacts with programmer 24 to communicate with IMD 16. For example, the user may interact with programmer 24 to retrieve physiological or diagnostic information from IMD 16, such as information relating to fluid accumulation and/or respiratory parameters. A user may also interact with programmer 24 to program IMD 16, e.g., select values for operational parameters of the IMD.

Figure 2:
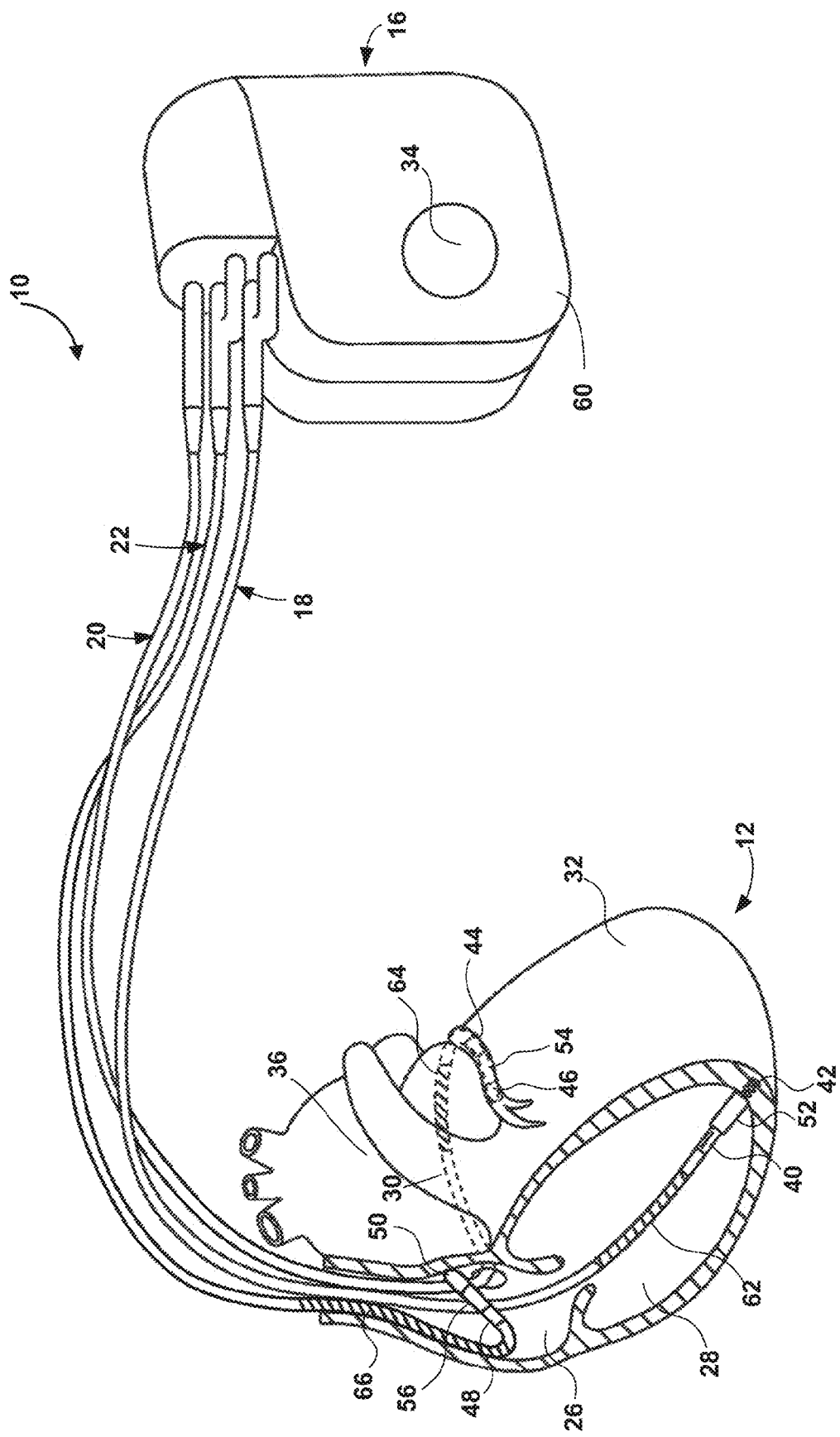
FIG. 2 is a conceptual diagram illustrating the implantable medical device (IMD) and leads of the system shown in FIG. 1 in greater detail.

FIG. 2 is a conceptual diagram illustrating IMD 16 and leads 18, 20, and 22 of system 10 in greater detail. Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 is electrically coupled to a respective one of the coiled conductors within the lead body of its associated lead 18, 20, 22, and thereby coupled circuitry within IMD 16.

IMD 16 includes one or more housing electrodes, such as housing electrode 34, which may be formed integrally with an outer surface of hermetically-sealed housing 60 of IMD 16 or otherwise coupled to housing 60. In some examples, housing electrode 34 is defined by an uninsulated portion of an outward facing portion of housing 60 of IMD 16. Other division between insulated and uninsulated portions of housing 60 may be employed to define two or more housing electrodes. In some examples, housing electrode 34 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12 and intrathoracic impedance of tissue in the body of patient 14.

In some examples, IMD 16 senses electrical signals attendant to the depolarization and repolarization of heart 12 via electrodes 34, 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 34. Additionally, any of the electrodes 40, 42, 44, 46, 48, 50, 62, 64 and 66 may be used in combination with housing electrode 34 to sense intrathoracic impedance of patient 14.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 34 in a unipolar configuration. Furthermore, IMD 16 may deliver cardioversion or defibrillation pulses to heart 12 via any combination of elongated electrodes 62, 64, 66, and housing electrode 34. Electrodes 62, 64, 66 may be fabricated from any suitable electrically conductive material, such as, but not limited to, platinum, platinum alloy or other materials known to be usable in implantable defibrillation electrodes.

Figure 3:
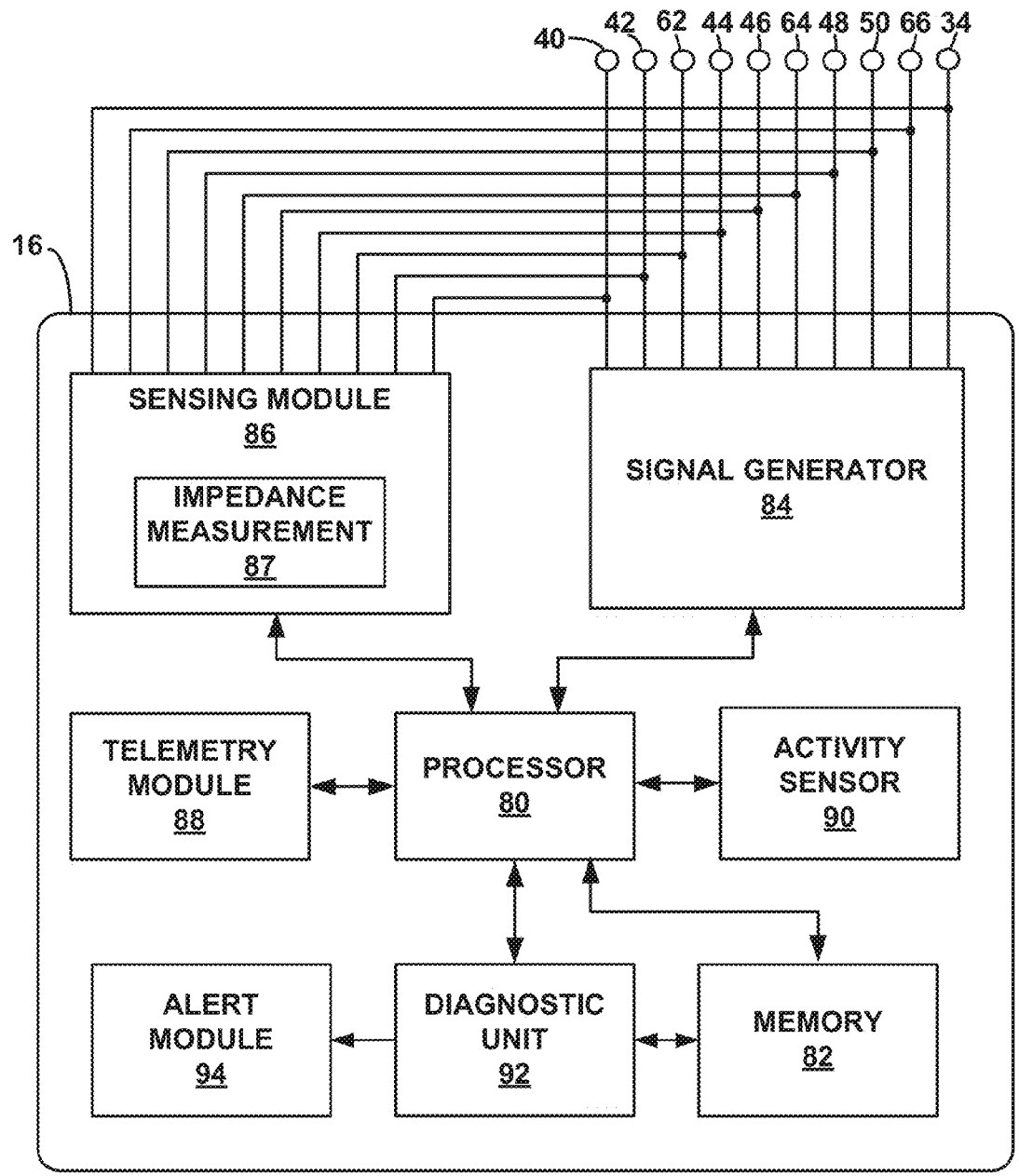
FIG. 3 is a functional block illustrating an example configuration of the IMD shown in FIG. 1.

FIG. 3 is a functional block diagram of one example configuration of IMD 16. In the illustrated example, IMD 16 includes a processor 80, memory 82, signal generator 84, electrical sensing module 86, telemetry module 88, activity sensor 90, diagnostic unit 92, and alert module 94. Memory 82 includes computer-readable instructions that, when executed by processor 80, cause IMD 16 and any other component of IMD 16 to perform various functions attributed to them herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy, e.g., pacing, cardioversion, or defibrillation, to heart 12 based on a selected one or more of therapy programs, which may be stored in memory 82. Specifically, processor 80 may control signal generator 84 to deliver electrical pulses with the amplitudes, pulse widths, frequency, or electrode polarities specified by the selected one or more therapy programs. Signal generator 84 is electrically coupled to electrodes 34, 40, 42, 44, 46, 48, 50, 62, 64, and 66, e.g., via conductors of the respective lead 18, 20, 22, or, in the case of housing electrode 34, via an electrical conductor disposed within housing 60 of IMD 16. A switch matrix may also be provided to connect signal generator 84 to a selected one or more of electrodes 34, 40, 42, 44, 46, 48, 50, 62, 64, and 66, and to cause the electrodes to have a selected polarity. In other examples, signal generator 84 delivers stimulation in the form of signals other than pulses, such as sine waves, square waves, or other substantially continuous time signals.

Electrical sensing module 86 monitors signals from at least one of electrodes 34, 40, 42, 44, 46, 48, 50, 62, 64 or 66 in order to monitor electrical activity of heart 12. Sensing module 86 may also include a switch module to select which of the available electrodes are used to sense the heart activity. In some examples, sensing module 86 includes one or more sensing channels, each of which may comprise an amplifier. In response to the signals from processor 80, the switch module within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 84 may be selectively coupled to housing electrode 34, or elongated electrodes 62, 64, or 66, with or instead of one or more of electrodes 40, 42, 44, 46, 48 or 50, e.g., for unipolar sensing of R-waves or P-waves in any of chambers 26, 28, 36, or 32 of heart 12.

In some examples, sensing module 84 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). Processor 80 may employ digital signal analysis techniques to characterize the digitized signals stored in memory 82 to detect and classify the patient's heart rhythm from the electrical signals. Processor 80 may detect and classify the patient's heart rhythm by employing any of the numerous signal processing methodologies known in the art.

If IMD 16 is configured to generate and deliver pacing pulses to heart 12, processor 80 may define atrial and ventricular pacing escape intervals, refractory periods during which sensed P-waves and R-waves are ineffective to restart timing of the escape intervals, the pulse widths of the pacing pulses, A-V intervals, and V-V intervals for cardiac resynchronization therapy (CRT). As another example, processor 80 may define a blanking period, and provide signals sensing module 86 to blank one or more channels, e.g., amplifiers, for a period during and after delivery of electrical stimulation to heart 12. As another example, processor 80 may control intervals for delivery of refractory period stimulation or cardiac potentiation therapy. The durations of these intervals may be determined by processor 80 in response to stored data in memory 82. Processor 80 may also determine the amplitude of the cardiac pacing pulses.

During pacing, escape interval counters within the pacer timing/control module of processor 80 may be reset upon sensing of R-waves and P-waves, or the delivery of a pacing pulse. The value of the count present in the escape interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect an arrhythmia event, such as an atrial or ventricular fibrillation or tachycardia. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia. IMD 16 may be configured to generate and deliver cardioversion or defibrillation pulses to heart 12 in response to a sensed tachyarrhythmia.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, and receive data from telemetry module.

In the example illustrated in FIG. 3, sensing module 86 includes an impedance measurement module 87. Processor 80 may control impedance measurement module 87 to periodically measure an electrical parameter to determine an impedance, such as an intrathoracic impedance. For an intrathoracic impedance measurement, processor 80 controls stimulation generator 84 to deliver an electrical signal between selected electrodes, and impedance module 87 to measure a current or voltage amplitude of the signal. In some examples, for collection of impedance measurements, signal generator 84 delivers signals that do not deliver stimulation therapy to heart 12, e.g., sub-threshold signals, due to, for example, the amplitudes or widths of such signals and/or the timing of delivery of such signals. Processor 80 may select any combination of electrodes 34, 40, 42, 44, 46, 48, 50, 62, 64, and 66, e.g., by using a switching module in signal generator 84 and/or sensing module 86. Impedance measurement module 87 includes sample and hold circuitry or other suitable circuitry for measuring resulting current and/or voltage amplitudes. Processor 80 determines an impedance value from the amplitude value(s) received from impedance measurement module 87.

In certain cases, IMD 16 measures intrathoracic impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components.

Processor 80 provides the measured impedances to diagnostic unit 92, which uses the received impedances to detect worsening heart failure in accordance with the techniques described in this disclosure. To avoid confusion, although diagnostic unit 92 is described as performing the monitoring and detecting techniques prescribed to IMD 16, it should be understood that these techniques may also be performed by processor 80. In some examples, diagnostic unit is a functional module provided or executed by processor 80. Accordingly, although processor 80 and diagnostic unit 92 are illustrated as separate modules in FIG. 3, processor 80 and diagnostic unit 92 may be incorporated in a single processing unit or equivalent circuitry.

When diagnostic unit 92 detects worsening heart failure of patient 14, diagnostic unit 92 activates alert module 94. In some examples, alert module 94 provides an alert to patient 14 to seek medical attention. That alert may be an audible or tactile alert. Alert module 94 may additionally or alternatively communicate with programmer 24 or another remote device via telemetry module 88 to provide an alert to patient 14 or a clinician.

Activity sensor 90 generates a signal that varies as a function of the activity level of patient 14. Activity sensor 90 may include one or more accelerometers that may be contained within or positioned on the housing of IMD 16, may be carried by one or more of leads 18, 20 and 22, or may be a remote sensor in wireless communication with IMD 16. Processor 80 or diagnostic unit 92 determines an activity level of the patient based on the signals received from activity sensor 90.

Respiratory parameters, such as respiration rate and depth, are affected by the activity level of the patient. Diagnostic unit 92 monitors the activity level of patient 14. In particular, for a determination of whether respiratory parameters indicate worsening of heart failure, diagnostic module 92 accounts for the affect of activity level on the respiratory parameters. In some examples, diagnostic module 92 measures respiratory parameters only when a patient is within an activity level range, e.g., at rest or otherwise below a threshold activity level. In other examples, diagnostic module 92 determines and then uses different respiratory parameter baseline values for different activity levels. In this manner, respiration may be used to detect worsening heart failure at any time, rather than when the patient is within a particular activity level range.

Figure 4:
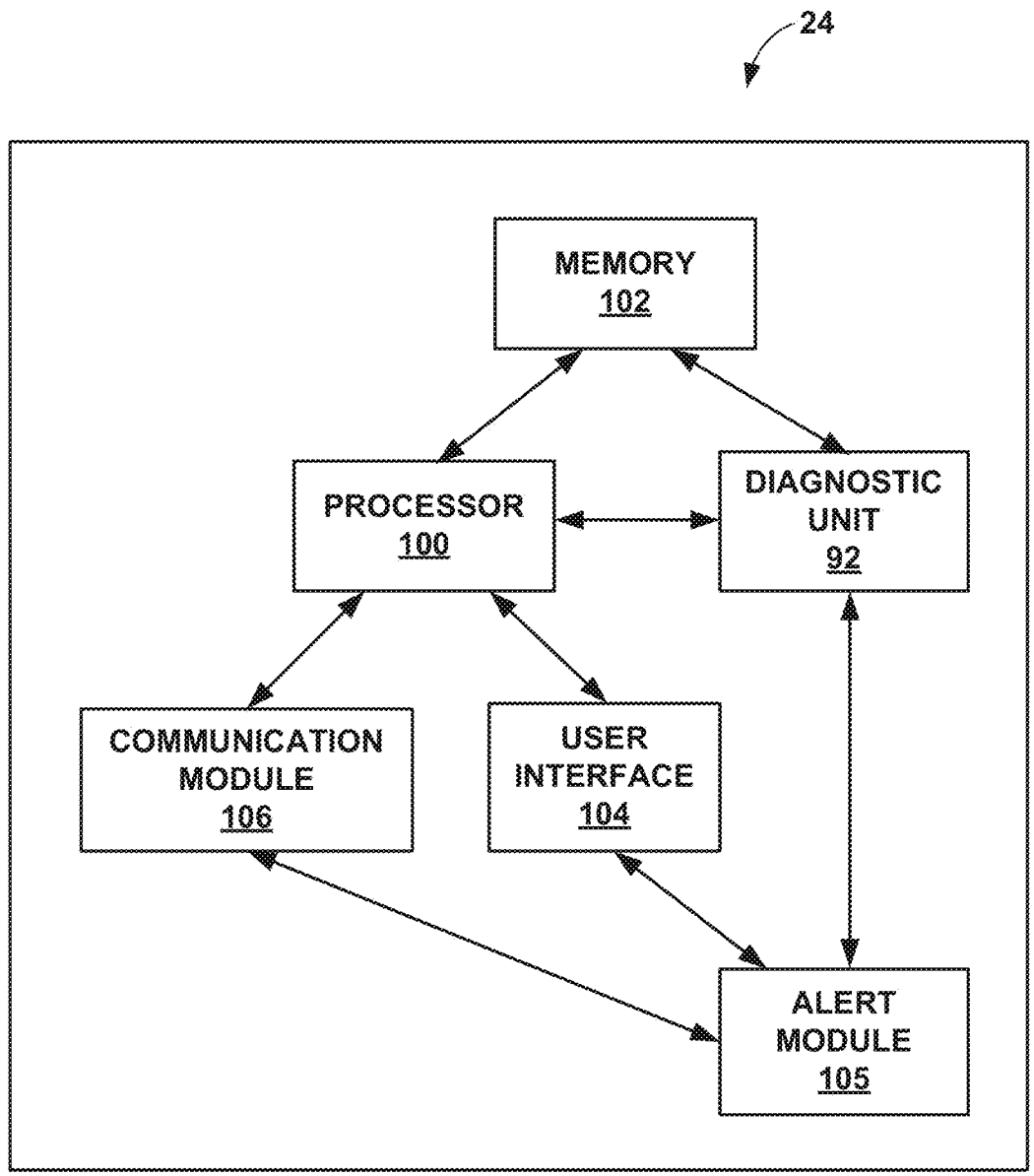
FIG. 4 is a functional block diagram illustrating an example configuration of the programmer shown in FIG. 1.

FIG. 4 is block diagram illustrating an example configuration programmer 24. In the example of FIG. 4, programmer 24 includes processor 100, memory 102, user interface 104, alert module and communication module 106. Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may include any fixed or removable magnetic, optical, or electrical media, such as RAM, ROM, CD-ROM, hard or floppy magnetic disks, EEPROM, or the like. Memory 102 may store program instructions that, when executed by processor 100, cause programmer 24 and any component thereof to provide the functionality ascribed to them herein.

A user of programmer 24 interacts with programmer 24 via user interface 104. User interface 104 includes a display to present a graphical user interface to a user, and a keypad or another mechanism for receiving input from a user. In some examples, user interface 104 includes a touch screen display.

Programmer 24 may communicate wirelessly with IMD 16, such as using RF communication or proximal inductive interaction. This wireless communication is possible through the use of communication module 106, which may be coupled to an internal antenna or an external antenna. An external antenna that is coupled to programmer 24 may correspond to the programming head that may be placed over heart 12. Communication module 106 may be similar to telemetry module 88 of IMD 16 (FIG. 3). Communication module 106 may also be configured to communicate with another computing device via wireless communication techniques, or direct communication through a wired, e.g., network, connection.

In some examples, IMD 16 detects worsening heart failure using any of the techniques described herein, and provides an indication of worsening heart failure to programmer 24. In response to receiving such an indication via communication module 106, processor 100 may control an alert module 105 to provide an alert of worsening heart failure to the patient, a clinician, or other users. In some examples, alert module 105 provides the alert to a user of programmer 24 via user interface 104. In some examples, alert module 105 provides the alert of worsening heart failure to one or more other computing devices via communication module 106 and a network.

Alerts provided via user interface 104 may include audible, visual, or tactile alerts. For example, user interface 104 may emit a beeping sound, display a text prompt, cause various buttons or screens to flash, or vibrate to alert patient 14 or another user that a heart failure decompensation event may be likely to occur. Patient 14 may then seek medical attention, e.g., check in to a hospital or clinic, to receive appropriate treatment, or the other user may instruct patient 14 to do so.

In the example illustrated in FIG. 4, programmer 24 includes diagnostic unit 92, which provides functionality as described above with respect to FIG. 3 and elsewhere herein. In such examples, diagnostic unit 92 receives impedance measurements (and in some cases patient activity levels) from IMD 16 via wireless communication provided by communication module 106. Diagnostic unit 92 processes the impedance measurements (and in some cases patient activity levels) to detect worsening heart failure in the manner described herein. Upon detecting worsening heart failure, diagnostic unit 92 control alert module 105 to provide an alert to a user. Diagnostic unit 92, although illustrated as a separate module in FIG. 4, may be incorporated in a single processing unit with processor 100 or functional module executed or provided by processor 100.

Although illustrated and described in the context of examples in which programmer 24 is able to program the functionality of IMD 16, in other examples a device capable of communicating with IMD 16 and providing functionality attributed to programmer 24 herein need not be capable of programming the functionality of the IMD. For example, an external home or patient monitor may communicate with IMD 16 for any of the purposes described herein, but need not independently be capable of programming the functionality of the IMD. Such as a device may be capable of communicating with other computing devices via a network, as discussed in greater detail below.

Figure 5:
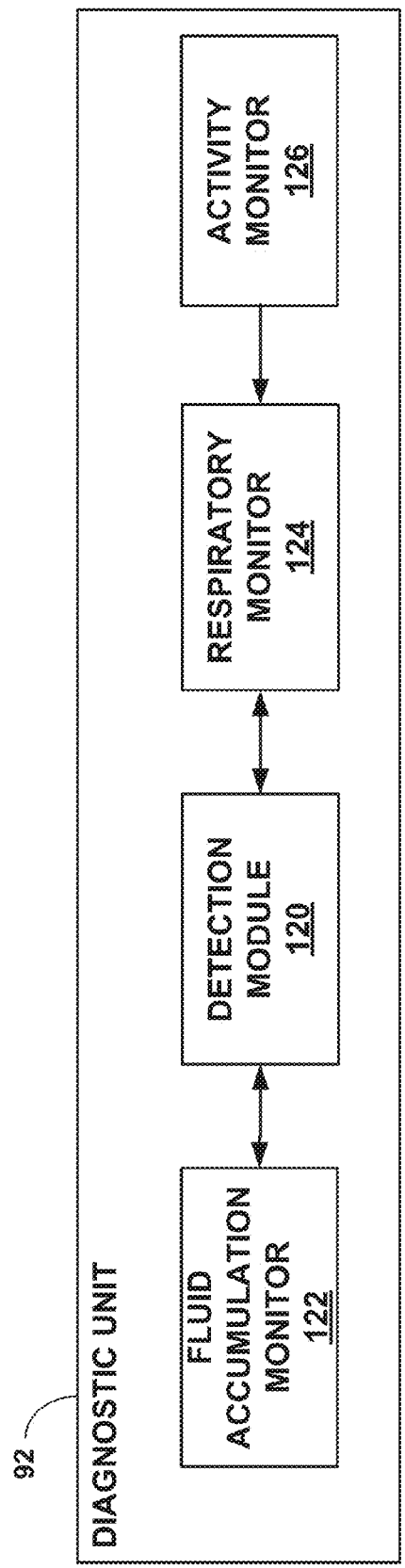
FIG. 5 is a functional block diagram illustrating an example configuration of a diagnostic unit shown in FIG. 3 and FIG. 4.

FIG. 5 is a block diagram of an example configuration of diagnostic unit 92. As shown in FIG. 5, diagnostic unit 92 includes multiple components including detection module 120, fluid accumulation monitor 122, respiratory monitor 124, and activity monitor 126. Because either IMD 16 or programmer 24 may be configured to include diagnostic unit 92, modules 120, 122, and 124 (and their sub-modules described below with reference to FIGS. 6 and 7) may be implemented in one or more processors, such as processor 80 of IMD 16 or processor 100 of programmer 24. The modules of diagnostic unit 92 (and their sub-modules described below with reference to FIGS. 6 and 7) may be embodied as one or more hardware modules, software modules, firmware modules, or any combination thereof. Although not illustrated in FIG. 5, the modules and sub-modules of diagnostic unit 92 may have access to memory 80 or 102 for buffering or storing any of the values discussed with reference to FIGS. 5-7, e.g., at locations accessible by and known to these modules.

Fluid accumulation monitor 122 monitors the intrathoracic impedance of patient 14, and outputs values relating to a degree of fluid accumulation to detection module 120. Respiratory monitor 124 monitors the intrathoracic impedance and outputs values for one or more respiratory parameters to detection module 120. For example, respiratory monitor 124 may analyze impedance values received from processor 80 to determine one or both of the respiration rate and volume of patient 14, and provide these values to detection module 120. Fluid accumulation monitor 122 and respiratory monitor 124 are configured to operate on the same intrathoracic impedance values.

Activity monitor 126 determines an activity level of patient 14 based on signals received from activity sensor 90. Activity monitor 126 provides the activity levels, or an indication that the activity levels are within a specified range, to respiratory monitor 124. In some examples, respiratory monitor 124 monitors the intrathoracic impedance and outputs values for one or more respiratory parameters to detection module 120 only when the activity levels are within a specified range, e.g., patient 14 is resting.

Detection module 120 processes data received from fluid accumulation monitor 122 and respiratory monitor 124 to detect worsening heart failure in patient 14. If detection module 120 detects worsening heart failure, diagnostic module 92 provides an indication of worsening heart failure to alert module 94 or 105. The alert module then provides an alert to a user.

In some examples, detection module 120 first receives from fluid accumulation monitor 122 current fluid index values and corresponding threshold values. When the fluid index value exceeds the threshold value, indicating fluid buildup, detection module 120 then receives current respiratory parameter values and corresponding reference or threshold values from respiratory monitor 124. Detection module 120 compares the current values to the reference or threshold values. If the comparison indicates dyspnea, e.g., if respiration rate is above a threshold determined based on a baseline rate and respiration volume is below a threshold determined based on a baseline volume, detection module 120 invokes alert module 94 and/or alert module 105. Otherwise, detection module 120 continues to collect impedance data to monitor the fluid status and one or more respiratory parameters.

In other words, detection module 120 may monitor fluid accumulation from fluid accumulation module 122 alone until the fluid accumulation indicates worsening heart failure. At that point, detection module 120 may begin monitoring respiratory parameters from respiratory module 124. Detection module 120 may determine whether the respiratory parameters indicate worsening heart failure, i.e., confirm the determination made based on fluid accumulation alone.

Figure 6:
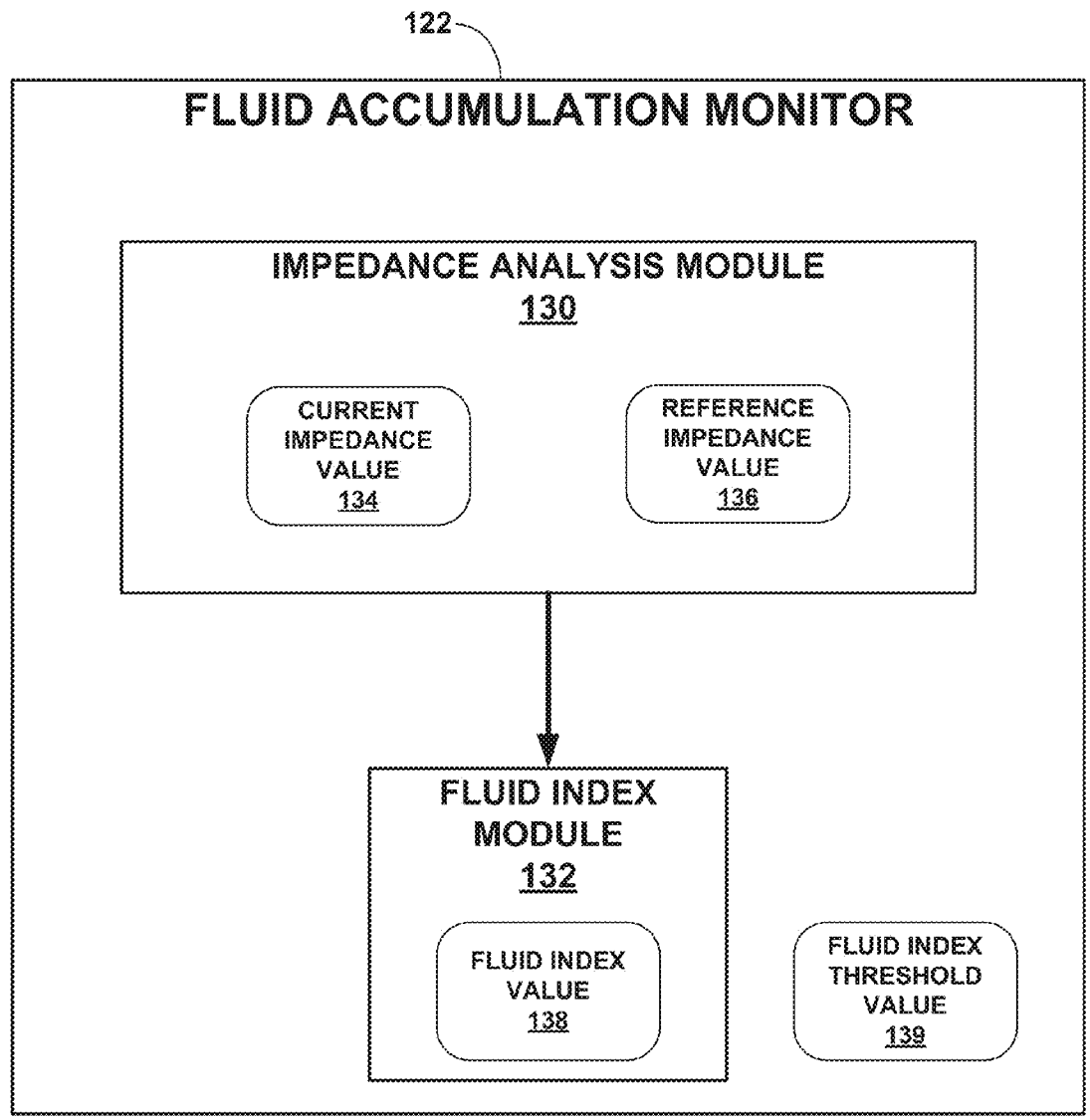
FIG. 6 is functional block diagram illustrating an example configuration of a fluid status monitor shown in FIG. 5.

FIG. 6 is a block diagram of an example configuration of fluid accumulation monitor 122. As shown in FIG. 6, fluid accumulation monitor 122 includes an impedance analysis module 130 and a fluid index module 132. In general, fluid accumulation monitor 122 periodically receives intrathoracic impedance measurements from processor 80, and analyzes the received measurements to determine a current impedance value 134 and a reference impedance value 136.

In some examples, impedance analysis module 130 determines current impedance value based 134 based on a plurality of impedance values received from processor 80 over a period of time. In such an example, impedance measurement module 87 (FIG. 3) may be configured to obtain a plurality of voltage or amplitudes values over the course of seconds, minutes, hours, or days. Processor 80 then processes the current or amplitude values to generate corresponding impedance values. Impedance analysis module 130 determines current impedance value 134 based on the received impedance values. Impedance analysis module 130 may determine current impedance value 134 as the average, median, mode, or the like of the received impedance values.

Impedance measurement module 87 and/or processor 80 (FIG. 3) measure impedance values on an hourly basis, daily basis, weekly basis, or other periodic interval. In one example, impedance measurement module 87 measures impedance values during a particular portion of a day, such as every twenty minutes during the afternoon. In some examples, impedance analysis module 130 determines a current impedance value 136 as an average or median of a plurality of such measured values, e.g., a daily average. Current impedance module 130 may utilize a buffer to store a plurality of measured impedance values to determine current impedance value 136. In other examples, current impedance value 136 is a single, most recently measured impedance value.

Impedance analysis module 130 also determines reference impedance value 136 based on impedance values received from impedance measurement module 87 and/or processor 80. However, the impedance values which impedance analysis module 130 uses to determine reference impedance value 136 may be different than those used to determine current impedance value 134. In some examples, impedance analysis module 130 generates a reference impedance value 136 based on the current impedance values 134 determined over time.

For example, impedance analysis module 130 may compare current impedance value 134 to a previous current impedance value, and determine a new reference impedance value 136 based on the comparison. Impedance analysis module 130 may generate a new reference impedance value 136 based on the prior reference impedance value. In some examples, impedance analysis module 130 increments or decrements reference impedance value 136 by a predetermined or variable amount based on whether current impedance value 134 is greater than a previous current impedance value.

Fluid index module 132 determines fluid index value 138 based on current impedance value 134 and reference impedance value 136. Fluid index value 138 increases and decreases inversely with respect to intrathoracic impedance in patient 14. In some examples, fluid index module 132 increments fluid index value 138 by the difference between current impedance value 134 and reference impedance value 136 when the current impedance value is less than the reference impedance value for a particular measurement interval. In some examples, fluid index module 132 decrements fluid index value 138 when the current impedance value is greater than the reference impedance value for a particular measurement interval. The amount of the decrement may be the difference between current impedance value 136 and reference impedance value 138, or a predetermined value. In some examples, fluid index module 132 sets fluid index value 138 to zero when the current impedance value is greater than the reference impedance value.

In some examples, fluid status monitor module may determine current impedance value 134, reference impedance value 136 and fluid index value 138 using any of the techniques described in U.S. application Ser. No. 12/184,149, filed Jul. 31, 2008, by Sarkar et al., entitled "DETECTING WORSENING HEART FAILURE BASED ON IMPEDANCE MEASUREMENTS," and/or U.S. application Ser. No. 10/727,008, filed on Dec. 3, 2003, by Stadler et al., entitled "METHOD AND APPARATUS FOR DETECTING CHANGE IN INTRATHORACIC IMPEDANCE." Each of these preceding applications is incorporated herein by reference in its entirety.

Fluid accumulation monitor 122 compares fluid index value 138 to a fluid index threshold value 139. Fluid index threshold value 139 may be predetermined and, in some examples, programmed by a physician using programmer 24.

Based on the comparison, fluid accumulation monitor 122 provides an indication to detection module 120, e.g., sets a flag, that indicates the status of the fluid accumulation, e.g., whether or not fluid index value 138 exceeds fluid index threshold value 139. Detection module 120 determines whether the fluid accumulation indicates worsening heart failure based on this indication from fluid accumulation monitor 122. In other words, detection module 120 determines that fluid accumulation indicates worsening heart failure in response to receiving an indication that index value 138 exceeds threshold value 139 from fluid accumulation monitor 122. As previously described, detection module 120 also begins to consider one or more respiratory parameters of patient 14 in response to such an indication from fluid accumulation monitor 122.

Figure 7:
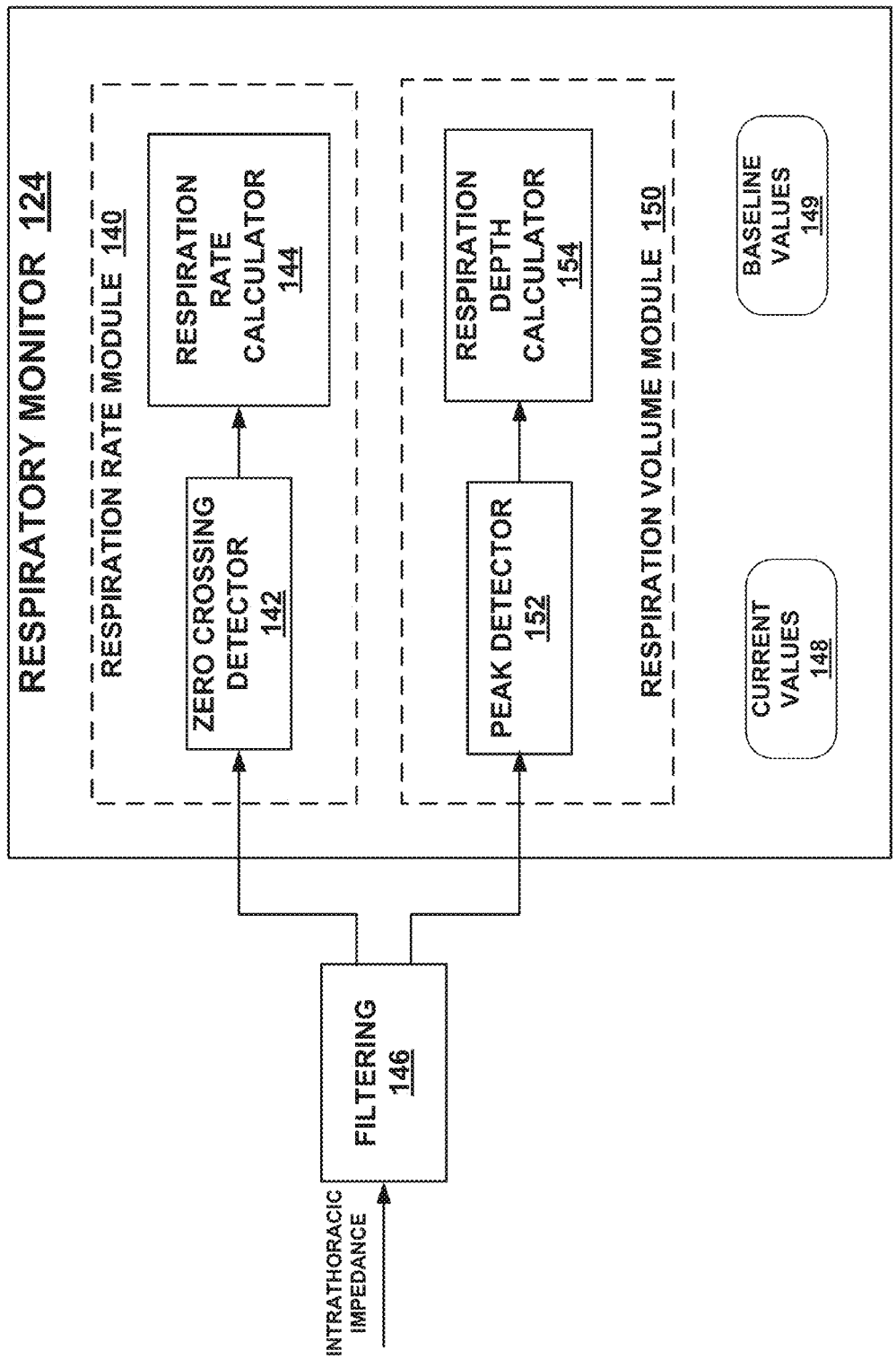
FIG. 7 is a functional block diagram illustrating an example configuration of a respiratory monitor shown in FIG. 5.

FIG. 7 is a block diagram of an example configuration of respiratory monitor 124. In the illustrated example, respiratory monitor 124 includes respiration rate module 140 and respiration volume module 150. In other examples, respiratory monitor 124 includes only one of respiration rate module 140 and respiration volume module 150.

Respiration rate module 140 and respiration volume module 150 both operate on intrathoracic impedance values measured by impedance measurement module 87. Thus, each of respiration rate module 140 and respiration volume module 150 are shown in FIG. 7 as receiving filtered intrathoracic impedance data from a filtering module 146. Filtering module 146 provides bandpass filtering for eliminating direct current (DC) components and other low and high frequency components from the impedance signal that are not of interest. Filtering module 146 is representative of a variety of modules that may be included in various examples to condition the impedance data for analysis for determining the respiration rate and volume of patient 14. Although not illustrated in FIG. 6, similar modules may also condition impedance data for analysis by fluid accumulation monitor 122. For example, a filtering module may provide low pass filtering to provide DC components of the impedance data to fluid accumulation monitor 122.

Respiration rate monitor 140 may include a zero crossing detector 144 and respiration rate calculator 146. Zero crossing detector 144 processes the filtered signal to identify zero crossings in the signal. Respiration rate calculator 146 determines a respiration rate based on the cycles in the signal, which is indicated by the number of zero crossings detected by zero crossing detector 146. For example, respiration rate calculator 146 may determine the respiration rate as the reciprocal of the number of cycles. Respiratory monitor 124 may store the respiration rate determined by calculator as a current value 148.

Zero crossing detector 144 may be calibrated following implant of IMD 16. This is because the impedance signal does not "per se" have zero crossings since a value of zero would indicate no resistance at all. Accordingly, zero crossing detector 144 is calibrated to detect instances when the impedance signal crosses a predetermined value. The predetermined value may be, as an example, a mean of the intrathoracic impedance signal over a period of time.

Respiration volume module 150 includes peak detector 152 and respiration depth calculator 154. Peak detector 152 processes filtered intrathoracic impedance signal to identify maxima and minima of the signal. Peak detector 152 may employ any known technique for peak detection in a signal to detect the maximum and minimum values.

Respiration depth calculator 154 determines the differences between adjacent maximum values and minimum values as the respiration depth. The differences are proportional to tidal volume. Respiratory monitor 124 stores the current respiration depth, or an average of a predetermined number of respiration depths, as a current value 148.

Respiratory monitor 124 also stores baseline values 149 for both respiration rate and respiration depth. Respiratory monitor 124 determines baseline values 149 in the same manner as current values 148, e.g., at or shortly after implant of IMD 16. Baseline values 149 may be determined at the request of a clinician and while a clinician supervises patient 14 to confirm that the baseline values actually represent the baseline condition of the patient. In examples in which respiratory monitor 124 determines current values 148 when patient 14 is within a particular activity level as indicated by activity monitor 126, e.g., at rest, respiratory monitor 124 may similarly determine baseline values 149 when patient 14 is within the particular activity level as indicated by activity monitor 126.

Respiratory monitor 124 compares current values 148 for respiration rate and volume to baseline values 149. Based on the comparison, respiratory monitor 124 provides an indication to detection module 120, e.g., sets a flag, that indicates the status of the respiratory parameters, e.g., whether or not the respiratory parameters have crossed respective thresholds, and thus indicate worsening heart failure. In some examples, respiratory monitor 124 provides such an indication when a current value 148 of respiration rate is at least a threshold value greater than the baseline value 149 for the respiration rate, and a current value 148 of respiration volume is at least a threshold value less than the baseline value 149 for the respiration volume. In other examples, respiratory monitor 124 provides such an indication when either rate or volume satisfies their respective requirement.

Detection module 120 determines whether the breathing parameters indicate worsening heart failure based on this indication from respiratory monitor 124. In other words, detection module 120 determines that the respiratory parameters indicate worsening heart failure in response to receiving an indication that the current values 148 for respiration rate and volume are sufficiently above and below, respectively, their baseline values 149. Detection module 120 may trigger an alert module 96, 105 to provide an alert in response to determining that the respiratory parameters indicate worsening heart failure.

Figure 8:
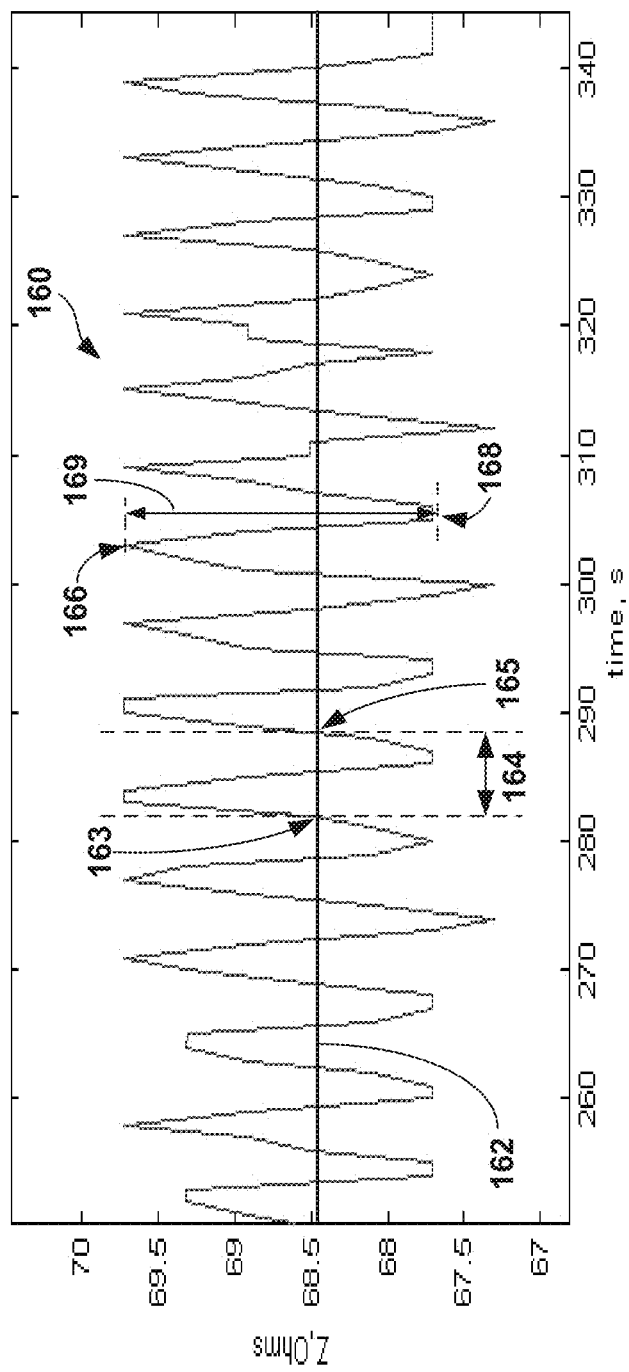
FIG. 8 is a graph illustrating an example impedance signal used by the IMD shown in FIG. 1 to detect worsening heart failure.

FIG. 8 is a graph illustrating an example impedance signal 160 and the determination of respiration rate and volume of patient 14. As shown in FIG. 8, impedance signal 160 is approximately a sinusoidal waveform that includes a plurality of periods. A horizontal axis 162 that may be used as a point of reference is also shown in FIG. 8. Horizontal axis 162 may represent a mean value calculated by respiration rate module 140 as previously described for determining the "zero crossings" of impedance signal 160.

FIG. 8 illustrates portions of signal 160 that are used for determining the respiration rate and volume of patient 14. Accordingly, various points of interest on signal 160 are labeled. Period 164 is the portion of signal 160 between two points 163 and 165 that cross horizontal axis 162. As previously described, the respiration rate of patient 14 can be determined by calculating the reciprocal of the number of periods or cycles of signal 160 over a specified period of time. Furthermore, the respiration volume 169 of patient 14 may be determined by determining a difference between a maximum 166 and minimum 168 that are adjacent.

Figure 9:
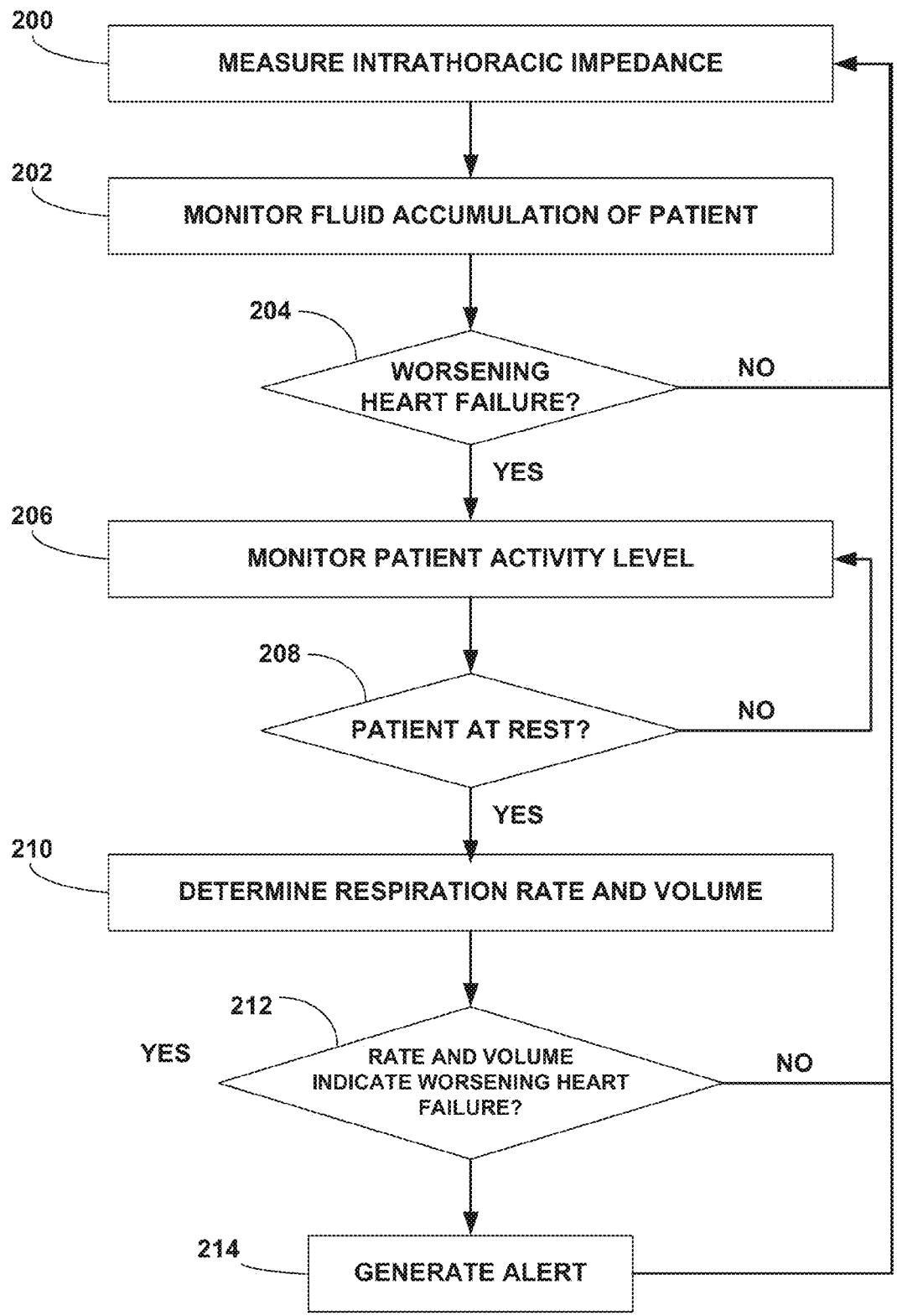
FIG. 9 is a flow diagram illustrating an example method that may be performed by the IMD or programmer shown in FIG. 1 to detect worsening heart failure in a patient.

FIG. 9 is a flow diagram illustrating an example method for detecting worsening heart failure in patient 14. The method may be performed entirely by IMD 16, or by a combination of IMD 16 and programmer 24. When the method is performed by IMD 16 and programmer 24, measurement of the intrathoracic impedance may be performed by IMD 16. For purposes of illustration only, it will be assumed in the subsequent description that diagnostic unit 92 and IMD 16 perform the method illustrated in FIG. 9. The method may be performed by any diagnostic unit(s) in any one or more devices, such as IMD 16 or programmer 24.

In the example shown in FIG. 9, IMD 16, e.g., impedance measurement module 87, collects intrathoracic impedance measurements (200). Fluid accumulation monitor 122 monitors the fluid accumulation of patient 14 based on the impedance measurements (202). Detection module 120 determines whether the fluid accumulation indicates worsening heart failure (204).

If the fluid accumulation does not indicate worsening heart failure (204), IMD 16 continues to collect impedance measurements and fluid accumulation monitor 122 continues to monitor the fluid accumulation (200, 202). If the fluid accumulation does indicate worsening heart failure (204), IMD 16 confirms the indication by beginning to monitor respiratory parameters.

In particular, activity monitor 126 monitors activity levels of patient (206). When activity monitor 126 determines patient is at rest, or otherwise within a desirable activity level range (208), respiratory monitor 124 determines values of one or more respiratory parameters, e.g., respiration rate and volume (210). Detection module 120 determines whether the respiratory parameters indicate, i.e., confirm, worsening heart failure (212).

If the respiratory parameters do not indicate worsening heart failure (212), IMD 16 continues to collect impedance measurements and fluid accumulation monitor 122 continues to monitor the fluid accumulation (200, 202). So long as fluid accumulation indicates worsening heart failure, respiratory monitor 124 determines values of the respiratory parameters, and detection module 120 determines whether the respiratory parameters indicate worsening heart failure (212). If the respiratory parameters do indicate worsening heart failure (212), alert module 96 generates an alert (214).

Because IMD 16 is configured to monitor the fluid accumulation and one or more respiratory parameters of patient 14 using the same intrathoracic impedance measurements, IMD 16 may monitor the fluid accumulation and respiratory parameters at the same time. In other words, although the steps of monitoring the fluid accumulation and respiratory parameters of patient 14 are shown in FIG. 9 as sequential steps, these steps may be performed substantially simultaneously. Thus, IMD 16 may monitor both the fluid status and respiratory parameters of patient 14 each time that impedance data is generated, but may use the respiratory parameters for making a decision only after the fluid accumulation indicates worsening heart failure. This may allow IMD 16 to have a respiratory parameter value, which may be a mean or median of a number of recent values, available for consideration upon the determination that the fluid accumulation indicates worsening heart failure.

Figure 10:
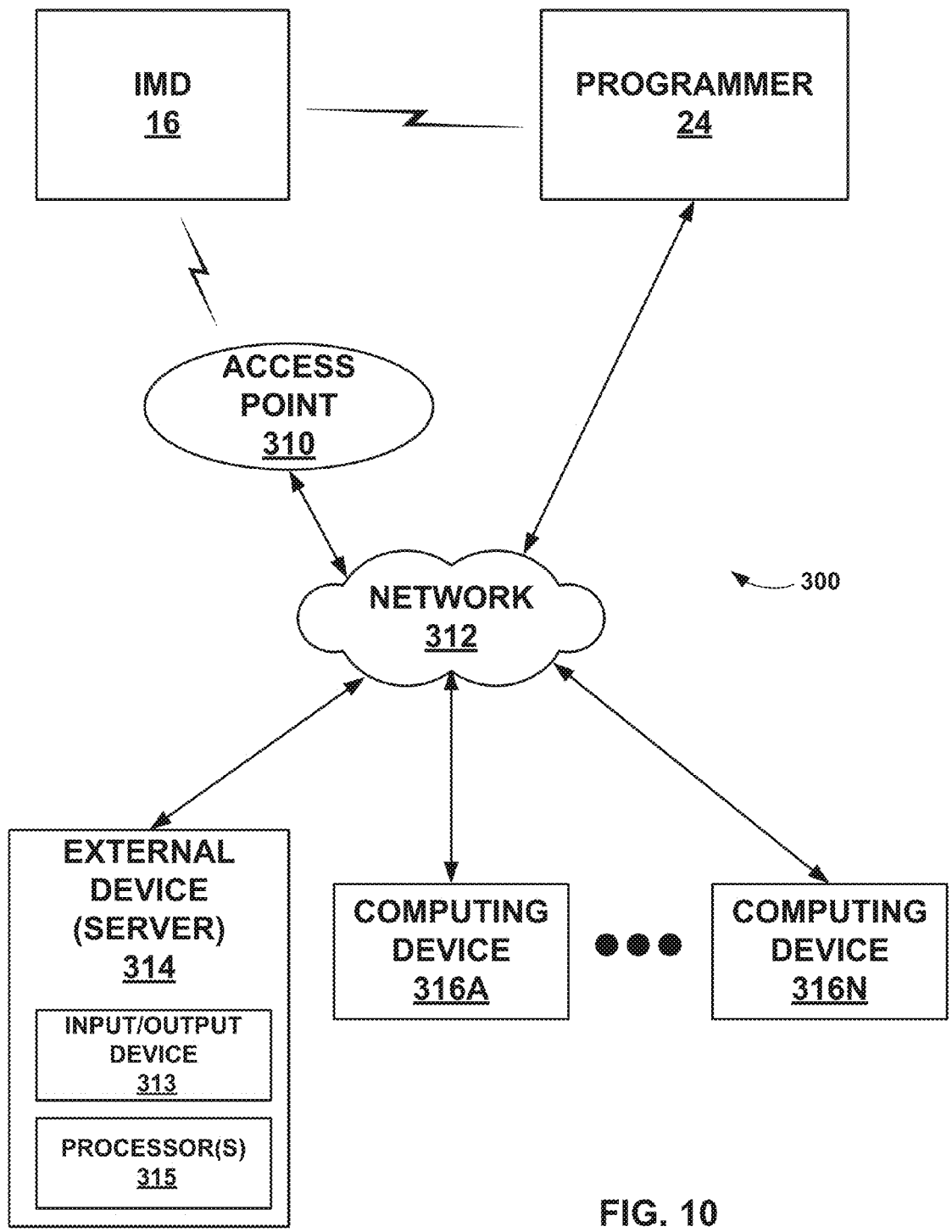
FIG. 10 is a block diagram illustrating an example system that includes an external device, such as a server, and one or more computing devices that are coupled to the IMD and programmer shown in FIG. 1 via a network.

FIG. 10 is a block diagram illustrating an example system 300 that includes an external device, such as a server 314, and one or more computing devices 316A-316N ("computing devices 316") that are coupled to IMD 16 and programmer 24 shown in FIG. 1 via a network 312. In this example, IMD 16 may use its telemetry module 88 to communicate with programmer 24 via a first wireless connection, and to communication with an access point 310 via a second wireless connection. In the example of FIG. 10, access point 310, programmer 24, server 314, and computing devices 316A-216N are interconnected, and able to communicate with each other, through network 312. In some cases, one or more of access point 310, programmer 24, server 314, and computing devices 316A-316N may be coupled to network 312 through one or more wireless connections. IMD 16, programmer 24, server 314, and computing devices 316A-216N may each comprise one or more processors, such as one or more microprocessors, DSPs, ASICs, FPGAs, programmable logic circuitry, or the like, that may perform various functions and operations, such as those described herein. For example, as illustrated in FIG. 10, server 314 may comprise one or more processors 315 and an input/output device 313, which need not be co-located.

Server 314 may, for example, monitor the fluid accumulation and one or more respiratory parameters of patient 14, e.g., based on impedance measurements received from IMD 16 and/or programmer 24 via network 312, to detect worsening heart failure of patient 14 using any of the techniques described herein. Server 314 may provide alerts relating to worsening heart failure of patient 16 via network 312 to patient 14 via access point 310, or to one or more clinicians via computing devices 316. In examples such as those described above in which IMD 16 and/or programmer 24 monitor the fluid status and one or more respiratory parameters of patient 14, server 314 may receive an alert from the IMD or programmer via network 312, and provide alerts to one or more clinicians via computing devices 316. Server 314 may generate web-pages to provide alerts and information regarding the primary and secondary diagnostic parameters, and may comprise a memory to store alerts and diagnostic or physiological parameter information for a plurality of patients.

Access point 310 may comprise a device that connects to network 312 via any of a variety of connections, such as telephone dial-up, digital subscriber line (DSL), or cable modem connections. In other examples, access point 310 is coupled to network 312 through different forms of connections, including wired or wireless connections. Network 312 comprises a local area network, wide area network, and/or global network, such as the Internet. System 300 may be implemented, in some aspects, with general network technology and functionality similar to that provided by the Medtronic CareLink® Network developed by Medtronic, Inc., of Minneapolis, Minn.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. However, one of ordinary skill in the art will appreciate that various modifications may be made to the described examples without departing from the scope of the claims. For example, although described primarily with reference to examples that provide an alert in response to detecting worsening heart failure, other examples may additionally or alternatively automatically modify a therapy in response to detecting worsening heart failure in the patient. The therapy may be, as examples, a substance delivered by an implantable pump, cardiac resynchronization therapy, refractory period stimulation, or cardiac potentiation therapy.

Furthermore, although described primarily with reference to examples in which impedance measurements are used to determine both fluid accumulation and respiratory parameters, in other examples one or both of fluid accumulation and respiratory parameters may be determined using another type of sensor. As one example, various cardiovascular pressures, such as an estimated or actual pulmonary artery diastolic pressure, may indicate fluid accumulation, and system may include a blood pressure sensor to monitor fluid accumulation. As another example, a piezoelectric sensor or accelerometer may be used to sense respiration and monitor respiratory parameters. These and other examples are within the scope of the following claims.

The invention claimed is:

1. A medical system comprising:
a fluid accumulation monitor configured to monitor thoracic fluid accumulation in a patient;
a detection module configured to detect worsening heart failure in the patient, wherein the detection module is configured to determine that the fluid accumulation indicates worsening heart failure in the patient; and
a respiratory monitor configured to monitor at least one respiratory parameter of the patient in response to the determination that the fluid accumulation indicates worsening heart failure,
wherein the detection module is configured to determine whether the respiratory parameter indicates worsening heart failure in the patient in response to the determination that the fluid accumulation indicates worsening heart failure.

2. The system of claim 1,
further comprising an impedance measurement module configured to collect intrathoracic impedance measurements from the patient via a plurality of electrodes,
wherein the fluid accumulation monitor is configured to monitor the fluid accumulation based on the impedance measurements, and the respiratory monitor is configured to monitor the at least one respiratory parameter based on the impedance measurements.

3. A medical system comprising:
a fluid accumulation monitor configured to monitor thoracic fluid accumulation in a patient;
a detection module configured to detect worsening heart failure in the patient, wherein the detection module is configured to determine that the fluid accumulation indicates worsening heart failure in the patient; and
a respiratory monitor configured to monitor at least one respiratory parameter of the patient in response to the determination that the fluid accumulation indicates worsening heart failure,
wherein the detection module is configured to determine whether the respiratory parameter indicates worsening heart failure in the patient in response to the determination that the fluid accumulation indicates worsening heart failure;
wherein the respiratory monitor continues to monitor the respiratory parameter and the detection module continues to determine whether the respiratory parameter indicates worsening heart failure so long as the fluid accumulation indicates worsening heart failure.

4. A medical system comprising:
a fluid accumulation monitor configured to monitor thoracic fluid accumulation in a patient;
a detection module configured to detect worsening heart failure in the patient, wherein the detection module is configured to determine that the fluid accumulation indicates worsening heart failure in the patient; and
a respiratory monitor configured to monitor at least one respiratory parameter of the patient in response to the determination that the fluid accumulation indicates worsening heart failure,
wherein the detection module is configured to determine whether the respiratory parameter indicates worsening heart failure in the patient in response to the determination that the fluid accumulation indicates worsening heart failure;
wherein the respiratory monitor is configured to monitor respiration rate and respiration volume, and wherein the detection module is configured to determine whether both of the respiration rate and the respiration volume indicate worsening heart failure.

5. The system of claim 1,
wherein the fluid accumulation monitor changes a fluid index value that indicates fluid accumulation in the patient over time based on the impedance measurements, and
wherein the detection module determines that the fluid accumulation indicates worsening heart failure when the fluid index crosses a threshold.

6. The system of claim 1, further comprising an activity monitor that periodically determines an activity level of the patient, wherein the respiratory monitor monitors the respiratory parameter when the activity level is less than a threshold level.

7. A medical system comprising:
a fluid accumulation monitor configured to monitor thoracic fluid accumulation in a patient;
a detection module configured to detect worsening heart failure in the patient, wherein the detection module is configured to determine that the fluid accumulation indicates worsening heart failure in the patient; and
a respiratory monitor configured to monitor at least one respiratory parameter of the patient in response to the determination that the fluid accumulation indicates worsening heart failure, wherein the detection module is configured to determine whether the respiratory parameter indicates worsening heart failure in the patient in response to the determination that the fluid accumulation indicates worsening heart failure; and further comprising an alert module that provides an alert to a user if the respiratory parameter indicates worsening heart failure.

8. The system of claim 1, further comprising an implantable medical device, wherein the implantable medical device comprises the impedance measurement module, fluid accumulation monitor, respiratory monitor, and detection module.

9. The system of claim 8, wherein the implantable medical device comprises at least one of a pacemaker, cardioverter, or defibrillator.

10. A medical system comprising:
  means for monitoring thoracic fluid accumulation in a patient;
  means for determining that the fluid accumulation indicates worsening heart failure in the patient;
  means for monitoring at least one respiratory parameter of the patient in response to the determination that the fluid accumulation indicates worsening heart failure; and
  means for determining whether the respiratory parameter indicates worsening heart failure in the patient in response to the determination that the fluid accumulation indicates worsening heart failure.

11. The system of claim 10,
  further comprising means for collecting intrathoracic impedance measurements from the patient,
  wherein the means for monitoring the fluid accumulation comprises means for monitoring the fluid accumulation based on the impedance measurements, and the means for monitoring the at least one respiratory parameter comprises means for monitoring the at least one respiratory parameter based on the impedance measurements.

12. The system of claim 10, wherein the at least one respiratory parameter comprises respiration rate and respiration volume, and wherein the means for determining whether the respiratory parameter indicates worsening heart failure comprises means for determining whether both of the respiration rate and the respiration volume indicate worsening heart failure.

13. The system of claim 10, further comprising means for monitoring an activity level of the patient, wherein the means for monitoring the respiratory parameter comprises means for monitoring the respiratory parameter when the activity level is less than a threshold level.

14. The system of claim 10, further comprising means for providing an alert to a user if the respiratory parameter indicates worsening heart failure.

* * * * *